(12) United States Patent
Peterson et al.

(10) Patent No.: US 11,529,383 B2
(45) Date of Patent: Dec. 20, 2022

(54) BIOCHEMICAL SCAFFOLDS FOR MODULATING CELL FUNCTION

(71) Applicant: Next2Me, LLC, Oakland, CA (US)

(72) Inventors: Ralph L Peterson, Oakland, CA (US); Renee D Williman, Oakland, CA (US)

(73) Assignee: Next2Me, LLC, Oakland, CA (US)

( * ) Notice: Subject to any disclaimer, the term of this patent is extended or adjusted under 35 U.S.C. 154(b) by 17 days.

(21) Appl. No.: 17/732,639

(22) Filed: Apr. 29, 2022

(65) Prior Publication Data
US 2022/0257682 A1    Aug. 18, 2022

Related U.S. Application Data

(63) Continuation-in-part of application No. 16/116,539, filed on Aug. 29, 2018, now abandoned, which is a continuation-in-part of application No. 14/223,392, filed on Mar. 24, 2014, now abandoned.

(60) Provisional application No. 61/936,116, filed on Feb. 5, 2014.

(51) Int. Cl.
| | |
|---|---|
| *A61K 31/4415* | (2006.01) |
| *A61K 36/258* | (2006.01) |
| *A61K 31/51* | (2006.01) |
| *A61K 31/455* | (2006.01) |
| *A61K 31/525* | (2006.01) |
| *A61K 36/185* | (2006.01) |
| *A61K 36/254* | (2006.01) |
| *A61K 36/74* | (2006.01) |
| *A61K 36/81* | (2006.01) |
| *A61K 36/31* | (2006.01) |
| *A61K 31/519* | (2006.01) |
| *A61K 31/197* | (2006.01) |
| *A61K 31/4188* | (2006.01) |

(52) U.S. Cl.
CPC .......... *A61K 36/258* (2013.01); *A61K 31/197* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 36/185* (2013.01); *A61K 36/254* (2013.01); *A61K 36/31* (2013.01); *A61K 36/74* (2013.01); *A61K 36/81* (2013.01)

(58) Field of Classification Search
CPC .............. A61K 36/258; A61K 31/4415; A61K 36/254; A61K 31/51
See application file for complete search history.

(56) References Cited

FOREIGN PATENT DOCUMENTS

CA    2609821 A1 * 11/2006 ........... A61K 9/0056

OTHER PUBLICATIONS

Pershin, S.M. Harmonic Oscillations of the Concentration of H-Bonds in Liquid Water; Laser Spectroscopy, vol. 16, No. 8, pp. 1184-1190. (Year: 2006).*

* cited by examiner

*Primary Examiner* — Neil P Hammell
*Assistant Examiner* — Paul C Martin
(74) *Attorney, Agent, or Firm* — Francis Law Group

(57) ABSTRACT

A method for modulating cellular activity in a subject, consisting essentially of the steps: (i) forming a liquid composition, (ii) subjecting the liquid composition to sequential harmonic oscillation to provide a liquid biochemical scaffold and, (iii) delivering a therapeutically effective amount of said liquid biochemical scaffold to said subject.

1 Claim, 5 Drawing Sheets

N2M BIOCHEMICAL SCAFFOLDS

| Modulator | Physiological Action/Reaction | Element/Compound |
|---|---|---|
| Krebs Cycle Modulator | 1) Induce and/or modulate at least one Krebs cycle metabolic reaction, process and/or pathway<br><br>2) Induce production of $CO_2$, acetyl-CoA, $FADH_2$ and adenosine triphosphate (ATP) | ashwaganda, eleuthero root (or extract), maca, an amino acid, e.g., L-arginine and L-citrulline, and vitamins $B_2, B_1, B_3, B_5$, and $B_9$ |
| Glutathione Modualator | 1) Induce the generation and/or proliferation of glutathione and/or a member of the glutathione family and, thereby, conversion of hydrogen peroxide to $H_2O$ and $O_2$<br><br>2) Induce the synthesis of catalase, i.e. an antioxidant | schisandra chinensis berry, damiana and epimedium and vitamine $B_2$<br><br>maca, nettles leaves, Fe and Cu, and vitamins $B_2, B_5, B_6$ and $B_7$ |
| Neurotransmitter Modulator | Induce the generation of electrochemical signals, i.e., neurotransmitters, and/or modulate the transmission thereof by and between neurons and, hence, cells | cannabidiol (DBD), epimedium, nettle leaf, maca, eleuthero root, Yohimbe, and vitamins $B_1$ and $B_6$ |

*FIG. 4A*

N2M BIOCHEMICAL SCAFFOLDS

| Modulator | Physiological Action/Reaction | Element/Compound |
|---|---|---|
| DNA Modulator | Support and/or enhance mitochondrial DNA activity | vitamin B$_{12}$ |
| Endocannabinoid System Modulator | Induce cell receptor activity; particularly, cannabinoid receptor activity | cannabidiol (CBD) |

FIG. 4B

BIOCHEMICAL SCAFFOLDS FOR MODULATING CELL FUNCTION

CROSS-REFERENCES TO RELATED APPLICATIONS

This application is a continuation-in-part of U.S. application Ser. No. 16/116,539, filed Aug. 29, 2018, now abandoned, which is a continuation-in-part of U.S. application Ser. No. 14/223,392, now abandoned, filed on Mar. 24, 2014, which claims the benefit of U.S. Provisional Application No. 61/936,116, filed on Feb. 5, 2014.

FIELD OF THE INVENTION

The present invention relates to compositions and methods for inducing cell activity. More particularly, the present invention relates to biochemical scaffolds and associated methods for inducing, supporting and/or enhancing cell activity and, thereby, function.

BACKGROUND OF THE INVENTION

As is well known in the art, optimal cell activity and, hence, function is essential to human existence. Cell activity and function is primarily dependent on the energy potential of a cell. Where cellular energy has been reduced, a cascade of undesirable cellular events can, and often times will, result. The noted cellular events typically result in one or more undesirable physiological characteristics, such as reduced stamina or endurance, and mental clarity.

Reduction of cellular energy can also result in dysfunction of various organs, e.g., heart and/or liver failure. When cellular energy approaches zero, cell death, i.e., apoptosis, is often encountered.

As is also well known in the art, cellular energy is directly dependent on various biochemical processes; particularly, cell respiration, i.e., metabolic reactions and processes that take place in the cells to convert biochemical energy from nutrients into adenosine triphosphate (ATP).

The metabolic reactions and processes, which are often referred to as a metabolic pathway, are typically embodied in the Krebs cycle.

Referring to FIG. 1, there is shown a schematic illustration of a Krebs cycle. As illustrated in FIG. 1, through catabolism of carbohydrates, fats, and proteins, a two carbon organic product, i.e., acetate in the form of acetyl-CoA, is produced. Acetyl-CoA and two equivalents of water ($H_2O$) are consumed during the citric acid cycle, producing two equivalents of carbon dioxide ($CO_2$) and one equivalent of HS-CoA.

In addition, one complete evolution of the Krebs cycle converts three equivalents of nicotinamide adenine dinucleotide ($NAD^+$) into three equivalents of reduced $NAD^+$ (NADH), one equivalent of ubiquinone (Q) into one equivalent of reduced ubiquinone ($QH_2$), and one equivalent each of guanosine diphosphate (GDP) and inorganic phosphate ($P_i$) into one equivalent of guanosine triphosphate (GTP). The NADH and $QH_2$ generated during the Krebs cycle are in turn used by the oxidative phosphorylation pathway to generate adenosine triphosphate (ATP).

A primary source of acetyl-CoA is carbohydrates, which are broken down by glycolysis to produce pyruvate. Pyruvate, in turn, is decarboxylated by the enzyme pyruvate dehydrogenase. The decarboxylated pyruvate generates acetyl-CoA, according to the following equation:

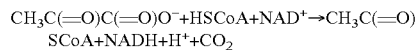

$$CH_3C(=O)C(=O)O^- + HSCoA + NAD^+ \rightarrow CH_3C(=O)SCoA + NADH + H^+ + CO_2$$

where;
$CH_3C(=O)C(=O)O^-$ represents pyruvate; and
$CH_3C(=O)SCoA$ represents acetyl-CoA.

Regulation of the Krebs cycle is largely dependent upon product inhibition and substrate availability. For example, NADH, a product of all dehydrogenases in the cycle (with the exception of succinate dehydrogenase) inhibits pyruvate dehydrogenase, isocitrate dehydrogenase, α-ketoglutarate dehydrogenase, and citrate synthase. Acetyl-CoA inhibits pyruvate dehydrogenase, while succinyl-CoA inhibits alpha-ketoglutarate dehydrogenase and citrate synthase.

Various elements and compositions have thus been employed to modulate one or more Krebs cycle processes to enhance cell activity and, thereby, generation of ATP. For example, calcium has been successfully employed to regulate the Krebs cycle. Calcium activates pyruvate dehydrogenase phosphatase, which, in turn, activates the pyruvate dehydrogenase complex. Calcium also activates isocitrate dehydrogenase and α-ketoglutarate dehydrogenase. This increases the reaction rate of many of the sequences in the cycle, and therefore increases flux throughout the pathway.

Citrate has also been employed as a feedback inhibitor. Citrate inhibits phosphofructokinase, i.e., an enzyme involved in glycolysis that catalyzes formation of fructose 1,6-bisphosphate, which is a precursor of pyruvate. This inhibits the formation of a high rate of flux when there is an accumulation of citrate.

Recent efforts have also been directed to the link between intermediates of the Krebs cycle and the regulation of hypoxia-inducible factors (HIF). HIF plays a role in the regulation of oxygen homeostasis, and is a transcription factor that targets angiogenesis, vascular remodeling, glucose utilization, iron transport, and apoptosis.

HIF is synthesized constitutively. Hydroxylation of at least one of two critical proline residues also mediates their interaction with the von Hippel Lindau E3 ubiquitin ligase complex, which targets them for rapid degradation. This reaction is catalyzed by prolyl 4-hydroxylases.

Various elements and compositions, such as fumarate and succinate, have thus been employed to inhibit the formation of prolyl hydroxylases and, thereby, stabilize HIF.

Although some of the noted elements and compositions have garnered some success in inducing Krebs cycle activity and, thereby cell activity and function (and, hence, enhancing ATP energy), there remains a need for improved biochemical formulations that effectively and readily enhance cell activity by inducing and/or modulating multiple Krebs cycle reactions and/or pathways.

Various formulations and efforts have also been employed to enhance cell activity and function by inducing or modulating other molecular actions, including inducing the generation and transmission of electrochemical signals, i.e., neurotransmitters, inducing DNA activity and inducing and/or modulating cell receptor activity.

Although the noted efforts have similarly garnered some success in enhancing cell activity and function, there still remains a need for biochemical scaffolds that effectively and readily enhance cell activity and, thereby optimal cell function, by inducing and modulating a plurality of seminal cell activities.

It would thus be desirable to provide improved biochemical scaffolds, i.e., formulations, and methods that enhance cell activity and function and, thereby, physical and mental function, by modulating multiple Krebs cycle reactions and/or pathways.

It would also be desirable to provide biochemical scaffolds and methods that enhance cell activity and function and, thereby, physical and mental function, by inducing (i) the generation of electrochemical signals, i.e., neurotransmitters, and modulating the transmission thereof by and between neurons, (ii) DNA activity, and (iii) cell receptor activity.

It would also be desirable to provide biochemical scaffolds that enhance cell activity and function and, thereby, physical and mental function, by inducing the generation and proliferation of selective cells and associated elements.

It is therefore an object of the present invention to provide biochemical scaffolds that enhance cell activity and function and, thereby, physical and mental function, by modulating at least one Krebs cycle metabolic reaction, process, and/or pathway.

It is another object of the present invention to provide biochemical scaffolds that enhance cell activity and function and, thereby, physical and mental function, by inducing the generation of neurotransmitters and modulating the transmission thereof by and between neurons.

It is another object of the present invention to provide biochemical scaffolds that enhance cell activity and function and, thereby, physical and mental function, by inducing cell receptor activity.

It is another object of the present invention to provide biochemical scaffolds that enhance cell activity and function and, thereby, physical and mental function, by inducing and/or modulating cell receptor activity.

It is another object of the present invention to provide biochemical scaffolds that enhance cell activity and function and, thereby, physical and mental function, by inducing and/or modulating endocannabinoid system activity.

It is another object of the present invention to provide biochemical scaffolds that support and/or enhance mitochondrial DNA activity.

It is another object of the present invention to provide biochemical scaffolds that enhance cell activity and function and, thereby, physical and mental function, by modulating a plurality of cell activities.

SUMMARY OF THE INVENTION

The present invention is directed to biochemical scaffolds and associated methods that induce and/or modulate at least one, more preferably, a plurality of molecular activities, including, without limitation, promoting and/or inducing (i) at least one Krebs cycle metabolic reaction, process and/or pathway, (ii) generation or proliferation of glutathione and/or a member of the glutathione family, (iii) generation or proliferation of at least one neurotransmitter, and/or modulating the transmission thereof by and between neurons, (iv) mitochondrial DNA activity, and (v) cell receptor activity.

In some embodiments of the invention, there are thus provided methods for modulating cellular activity of a subject. In one embodiment, the method for modulating cellular activity of a subject comprises:
 (i) providing a liquid composition comprising glycerin-based water, schisandra chinensis, eleuthero root, epimedium, maca root, cannabidiol (CBD), vitamin $B_1$, vitamin $B_2$, vitamin $B_3$, vitamin $B_5$, vitamin $B_6$, vitamin $B_7$, and vitamin $B_{12}$;
 (ii) subjecting the liquid composition to harmonic oscillation at a frequency in the range of 102 GHz to 250 GHz for a period of time in the range of 3 hours to 5 hours, wherein a liquid biochemical scaffold is provided; and
 (iii) delivering a therapeutically effective amount of the liquid composition to the subject.

In some embodiments of the invention, the method for modulating cellular activity of a subject comprises the steps of:
 (i) providing a liquid composition comprising glycerin-based water, schisandra chinensis, eleuthero root, epimedium, maca root, cannabidiol (CBD), vitamin $B_1$, vitamin $B_2$, vitamin $B_3$, vitamin $B_5$, vitamin $B_6$, vitamin $B_7$, and vitamin $B_{12}$;
 (ii) subjecting the liquid composition to sequential harmonic oscillation at a first frequency in the range of 0.9 kHz-1.5 kHz for a first period of time in the range of 3-60 minutes, a second frequency in the range of 9.5 kHz-10.5 kHz for a second period of time in the range of 3-60 minutes, a third frequency in the range of 9.5 kHz-11.0 kHz for a third period of time in the range of 3-60 minutes, a fourth frequency in the range of 0.01 kHz-0.03 kHz for a fourth period of time in the range of 3-60 minutes, and a fifth frequency in the range of 0.004 kHz-0.010 kHz for a fifth period of time in the range of 3-60 minutes, wherein a liquid biochemical scaffold is provided; and
 (iii) delivering a therapeutically effective amount of the liquid composition to the subject.

In some embodiments of the invention, the method for modulating cellular activity of a subject comprises the steps of:
 (i) providing a liquid composition comprising glycerin-based water, epimedium, stinging nettle, yohimbe, red Korean ginseng, eleuthero root, damiana, ashwagandha, maca root, vitamin $B_1$, vitamin $B_2$, vitamin $B_3$, vitamin $B_5$, vitamin $B_6$, vitamin $B_7$, vitamin $B_9$, and vitamin $B_{12}$;
 (ii) subjecting the liquid composition to sequential harmonic oscillation at a first frequency in the range of 0.9 kHz-1.5 kHz for a first period of time in the range of 3-60 minutes, a second frequency in the range of 9.5 kHz-10.5 kHz for a second period of time in the range of 3-60 minutes, a third frequency in the range of 9.5 kHz-11.0 kHz for a third period of time in the range of 3-60 minutes, a fourth frequency in the range of 0.01 kHz-0.03 kHz for a fourth period of time in the range of 3-60 minutes, and a fifth frequency in the range of 0.004 kHz-0.010 kHz for a fifth period of time in the range of 3-60 minutes, wherein a liquid biochemical scaffold is provided; and
 (iii) delivering a therapeutically effective amount of the liquid composition to the subject.

In a preferred embodiment, the therapeutically effective amount of the biochemical scaffold liquid composition delivered to the subject comprises in the range of approximately 0.0006 oz. to 0.018 oz. of the liquid composition.

According to the invention, the biochemical scaffolds of the invention promote and/or induce specific seminal biochemical activities in vivo through resonant transfer of retained energy signatures to biological tissue and, hence, endogenous cells thereof, whereby at least one of the following molecular activities are promoted and/or induced or, in some instances, supported: (i) at least one Krebs cycle metabolic reaction, process and/or pathway, (ii) generation or proliferation of glutathione and/or a member of the glutathione family, (iii) generation or proliferation of at least one neurotransmitter, and/or modulating the transmission thereof by and between neurons, (iv) mitochondrial DNA activity, and (v) cell receptor activity.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIGS. 4A and 4B are tables of biochemical scaffolds, according to the invention.

DETAILED DESCRIPTION OF THE PREFERRED EMBODIMENT

Figure 1:
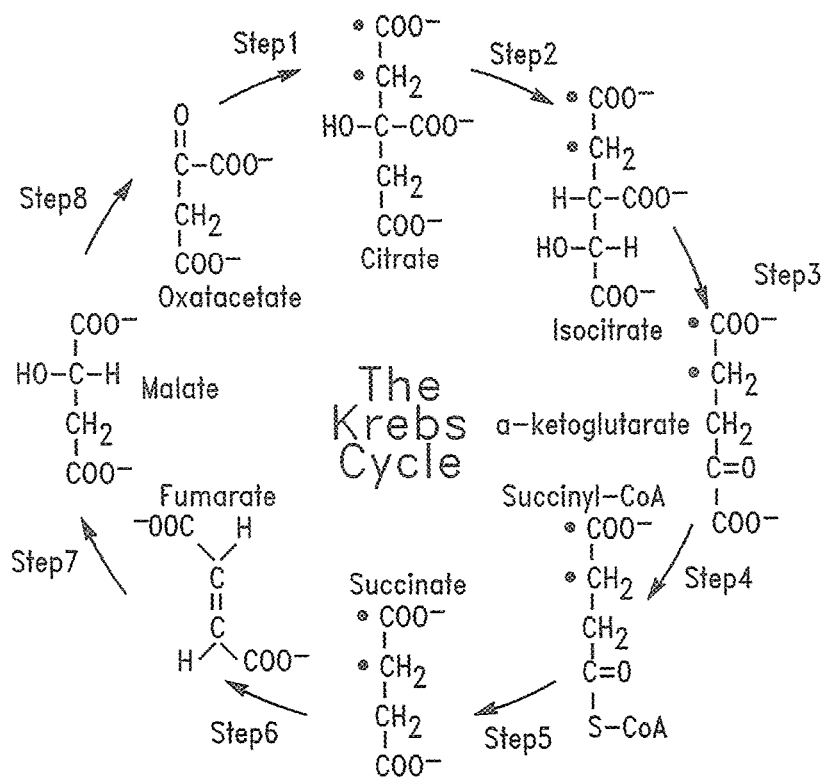
FIG. 1 is a schematic illustration of a Krebs cycle.
Figure 2:
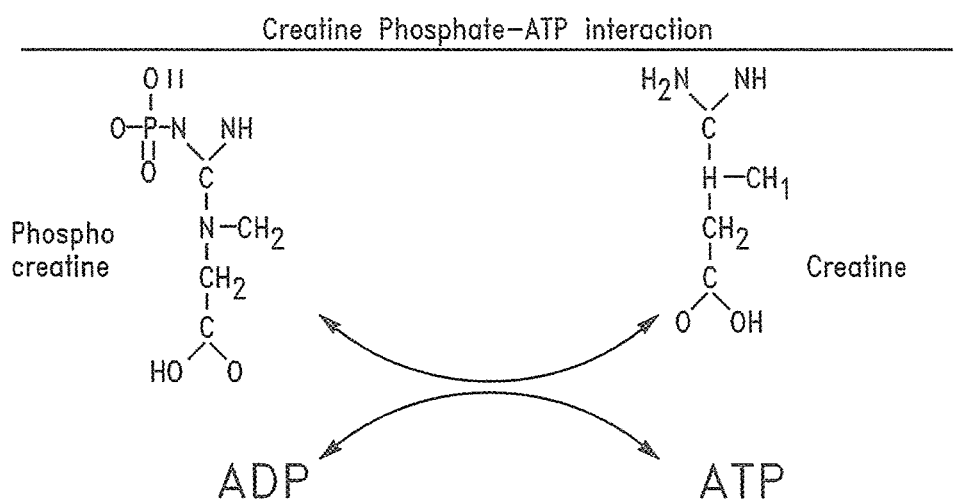
FIG. 2 is a schematic illustration of creatine phosphate-ATP interaction.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a", "an" and "the" include plural referents unless the content clearly dictates otherwise.

Definitions

The term "vibrational energy platform," as used herein, means and includes biologically targeted complex, stable, and efficient energetic blanks and glycerol water-soluble molecules, which, when programmed with a laser charged imprint of herbs, minerals, vitamins, amino acids, or pharmaceutical properties (creating energy-signature templates), help stimulate/enable/enhance vital cellular biochemical processes necessary to maintain homeostasis.

The term "biochemical agent" as used herein, means and includes any element, agent, drug, compound, composition of matter or mixture thereof comprising an energy signature component.

The terms "energy signature" and "energy signature component," are used interchangeably herein, mean and include the specific energetic or electromagnetic identity of a selective herb or biochemical agent and, hence, molecular structure(s) thereof when the herb or biochemical agent is exposed to radiation energy, such as radiation energy generated via harmonic oscillation. The terms "energy signature" and "energy signature component," as used interchangeably herein, also mean and include the properties and functions of an herb or biochemical agent associated with the energetic identity of the herb or biochemical agent.

The term "Krebs cycle modulator," as used herein, means and includes an element, agent, drug, compound, composition of matter or mixture thereof, including its formulation, which induces and/or modulates a Krebs cycle metabolic reaction, process and/or pathway, including, without limitation, Krebs cycle product inhibition and/or substrate availability. According to the invention, suitable Krebs cycle modulators comprise, without limitation, eleuthero root (or extract), maca, an amino acid, e.g., L-arginine and L-citrulline, and vitamins $B_2$, $B_1$, $B_3$, $B_5$, and $B_9$.

The term "neurotransmitter modulator," as used herein, means and includes an element, agent, drug, compound, composition of matter or mixture thereof, including its formulation, which induces the generation or proliferation of at least one neurotransmitter and/or modulates the transmission thereof by and between neurons and, hence, cells. According to the invention, suitable neurotransmitter modulators comprise, without limitation, stinging nettle leaf (also referred to herein as "stinging nettle"), maca, eleuthero root, yohimbe, vitamin $B_1$, and vitamin $B_6$.

The term "glutathione modulator," as used herein, means and includes an element, agent, drug, compound, composition of matter or mixture thereof, including its formulation, which induces the generation or proliferation of glutathione and/or the glutathione family, including, without limitation, glutathione peroxidase.

The term "glutathione modulator" also means and includes an element, agent, drug, compound, composition of matter or mixture thereof, including its formulation, which induces catalase synthesis.

According to the invention, suitable glutathione modulators comprise, without limitation, herbs, including, without limitation, schisandra chinensis berry, damiana, epimedium, maca, and stinging nettle leaf; metal ions including iron (Fe) and copper (Cu); and B-vitamins selected from the group comprising vitamins $B_2$, $B_5$, $B_6$, and $B_7$.

The term "DNA modulator," as used herein, means and includes an element, agent, drug, compound, composition of matter or mixture thereof, including its formulation, that induces and/or modulates mitochondrial DNA, including protecting and/or facilitating the repair of mitochondrial DNA. According to the invention, a suitable DNA modulator comprises, without limitation, vitamin $B_{12}$.

The term "endocannabinoid system modulator," as used herein, means and includes an element, agent, drug, compound, composition of matter or mixture thereof, including its formulation, which induces and/or modulates cell receptor activity; particularly, cannabinoid receptor activity, i.e., the activity of CB1 or CB2. According to the invention, a suitable endocannabinoid system modulator comprises, without limitation, cannabidiol (CBD).

The term "nuclear hormone receptor modulator," as used herein, means and includes an element, agent, drug, compound, composition of matter or mixture thereof, including its formulation, which induces and/or modulates cell receptor activity; particularly, nuclear hormone receptor activity, e.g., the activity of estrogen receptor-α (ERα), estrogen receptor-β (ERβ), androgen receptor (AR), and mineralocorticoid receptor (MR). According to the invention, a suitable nuclear hormone receptor modulator comprises, without limitation, red Korean ginseng.

The terms "cellular dysfunction" and "cell dysfunction" are used interchangeably herein and mean and include a reduction or impairment in physical structure or function of a cell.

The term "organ dysfunction", as used herein, means and includes a reduction or impairment in physical structure or function of a mammalian organ, including, without limitation, the cardiovascular vascular system (heart and lungs), digestive system (salivary glands, esophagus, stomach, liver, gallbladder, pancreas, intestines, colon, rectum, and anus), endocrine system (hypothalamus, pituitary gland, pineal body, thyroid, parathyroids, and adrenals), excretory system (kidneys, ureters, bladder, and urethra), immune system (lymphatic system, tonsils, adenoids, thymus, and spleen), integumentary system (skin, hair and nails), muscular system, nervous system (brain and spinal cord), reproductive system (ovaries, fallopian tubes, uterus, vagina, mammary glands, prostate, and penis), respiratory system (pharynx, larynx, trachea, bronchi, and diaphragm), and the skeletal system (bones, cartilage, ligaments, and tendons).

The terms "prevent" and "preventing" are used interchangeably herein, and mean and include reducing the frequency or severity of a disease, condition, dysfunction or disorder. The term does not require an absolute preclusion of the disease, condition, dysfunction, or disorder. Rather, this term includes decreasing the chance for disease occurrence.

The terms "treat" and "treatment" are used interchangeably herein, and mean and include medical management of a patient with the intent to cure, ameliorate, stabilize, or prevent a disease, pathological condition, dysfunction, or disorder. The terms include "active treatment", i.e., treatment directed specifically toward the improvement of a disease, pathological condition, dysfunction, or disorder, and "causal treatment", i.e., treatment directed toward removal of the cause of the associated disease, pathological condition, dysfunction, or disorder.

The terms "treat" and "treatment" further include "palliative treatment", i.e., treatment designed for the relief of symptoms rather than the curing of the disease, pathological condition, dysfunction, or disorder, "preventative treatment", i.e., treatment directed to minimizing or partially or completely inhibiting the development of the associated disease, pathological condition, dysfunction, or disorder, and "supportive treatment", i.e., treatment employed to supplement another specific therapy directed toward the improvement of the associated disease, pathological condition, dysfunction, or disorder.

The terms "pharmacological agent," "active agent" and "drug" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans, and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent," "active agent" and "drug" thus mean and include, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombotic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, and vasodilating agents.

The term "therapeutically effective", as used herein, means that the amount of a Krebs cycle modulator, glutathione modulator, neurotransmitter modulator, or DNA modulator and/or biochemical scaffold formed therefrom, or pharmacological or bioactive agent administered to a subject is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "delivery" and "administration" are used interchangeably herein, and mean and include providing a Krebs cycle modulator, glutathione modulator, neurotransmitter modulator or DNA modulator and/or biochemical scaffold formed therefrom to a subject through any method appropriate to deliver formulations and/or scaffolds to a subject. Non-limiting examples of delivery methods include oral, sublingual, nasal, direct injection, topical application, etc.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As indicated above, the present invention is directed to biochemical scaffolds and associated methods that induce and/or modulate at least one, more preferably, a plurality of molecular activities, including, without limitation, inducing (i) at least one Krebs cycle metabolic reaction, process and/or pathway, (ii) generation or proliferation of glutathione and/or a member of the glutathione family, (iii) generation or proliferation of at least one neurotransmitter, and/or modulating the transmission thereof by and between neurons, (iv) inducing and/or supporting mitochondrial DNA activity, and (v) cell receptor activity.

According to the invention, by virtue of the noted modulated molecular activities that are induced by the biochemical scaffolds of the invention, cellular activity and function and, thereby, physical and mental function, is significantly enhanced.

In a preferred embodiment of the invention, the biochemical scaffolds comprise two platforms (and components associated therewith): a vibrational energy platform and a bioenergetic platform.

In some embodiments of the invention, the bioenergetic platforms further comprise a liquid medium. According to the invention, the biochemical scaffold can comprise any suitable medium, such as a glycerol water solution (also referred to herein as "glycerin-based water"), and distilled water. In some embodiments, the liquid medium comprises oxygen enriched glycerin infused water molecules.

As set forth in priority U.S. application Ser. No. 14/223,392, in some embodiments, the biochemical scaffold comprises a glycerol water solution comprising at least 1200 mg/ml of glycerin.

In some embodiments of the invention, the bioenergetic platforms comprise at least one of the following modulators: a Krebs cycle modulator, glutathione modulator, neurotransmitter modulator, DNA modulator, or endocannabinoid modulator.

Thus, in some embodiments, the bioenergetic platforms comprise a Krebs cycle modulator and/or glutathione modulator and/or neurotransmitter modulator and/or DNA modulator and/or endocannabinoid modulator.

In some embodiments, the bioenergetic platforms comprise a plurality of Krebs cycle modulators, and/or glutathione modulators, and/or neurotransmitter modulators, and/or DNA modulators, and/or endocannabinoid modulators.

In a preferred embodiment of the invention, the Krebs cycle modulators induce and/or modulate a Krebs cycle metabolic reaction, process and/or pathway, including, without limitation, Krebs cycle product inhibition and/or substrate availability.

As set forth in FIG. 4A and discussed in detail below, in some embodiments, the Krebs cycle modulators also induce multiple Krebs cycle reactions and/or pathways, resulting in the production of $CO_2$, and/or acetyl-CoA, and/or $FADH_2$, and enhanced adenosine-5'-triphosphate (ATP) energy potential.

As set forth in Applicants' priority U.S. application Ser. Nos. 14/223,392 and 16/116,539, ATP is a multifunctional nucleoside triphosphate that is used as a coenzyme in cells. ATP is one of the end products of photophosphorylation and cellular respiration, and is used by structural proteins in many cellular processes, including biosynthetic reactions, motility, and cell division.

Mammalian mitochondria are organelles that produce more than 90% of cellular ATP. In addition to supplying ATP, i.e., cellular energy, mitochondria are also involved in other cellular mechanisms, including cellular differentiation, apoptosis, as well as cell cycle modulation and cell growth.

Mitochondria provide intracellular ATP via a process called glycolysis, which breaks down monosaccharides into ATP through a series of biochemical processes. Mitochondria contain, among other things, the Krebs cycle enzymes that are involved in heme biosynthesis and the electron transport chain, i.e., the Oxidative Phosphorylation pathway (OxPHOS) system. Due to the large flux of redox reactions necessary to maintain oxidative phosphorylation, mitochondria are the primary site of production of reactive oxygen species (ROS).

It has, however, been found that increased production of ROS and interference with the OxPhos system can cause cell cycle dysfunction and arrest.

The OxPHOS system is composed of five large multi-protein enzyme complexes, which collectively transform the reducing energy of NADH and $FADH_2$ to ATP. NADH ubiquinone oxidoreductase (Complex I) contains 45 different subunits, and succinate ubiquinone reductase (Complex II), ubiquinone-cytochrome c oxidoreductase (Complex III), cytochrome c oxidase (Complex IV), and the ATP synthase (Complex V) contain 4, 11, 13 and 16 subunits, respectively.

Four of the OxPHOS enzyme complexes (Complexes I, III, IV and V) have a dual genetic origin, i.e., they are composed of both nuclear DNA-encoded proteins and mitochondrial DNA-encoded proteins.

Transient ischemia (anoxia) results in the local production of extremely high levels of ROS, which can cause long term damage to mitochondria. In the initial phase of transient ischemia, oxygen is scarce, but tissue demands for ATP remain high, resulting in continued functioning of the OxPhos system except for the terminal reduction of oxygen to water by Complex IV. Therefore, reduced electron acceptors "upstream" of Complex IV accumulate to abnormally high levels.

Upon resupply of oxygen, these excess reduced carriers react directly with oxygen to generate highly toxic partially reduced oxygen species, which are capable of protein, lipid, and DNA modifying reactions. The resulting oxidative damage is deemed to occur mainly inside the mitochondrion, because such radicals are so reactive that they are short lived and cannot diffuse far before finding a target for reaction.

Accordingly, OxPHOS proteins and DNA are deemed the cellular molecules most affected by such oxidative stress. The resulting defects in DNA and OxPHOS proteins can, and in most instances will, result in continued increased production of ROS.

However, it has been found that modulating the OxPhos system and, thereby, ROS production, which can be achieved by the Krebs cycle modulators of the invention, oxidative stress of cells can be substantially reduced or eliminated.

As discussed in detail herein, in some embodiments of the invention, the Krebs cycle modulators comprise at least one herb selected from the group comprising, without limitation, schisandra chinensis berry, epimedium, stinging nettle, yohimbe, red Korean ginseng, eleuthero root (or extract), damiana, ashwagandha and maca, at least one amino acid, comprising, without limitation, L-arginine and L-citrulline, and at least one B vitamin selected from the group comprising vitamins $B_2$, $B_1$, $B_3$, $B_5$, $B_7$, $B_9$, and $B_{12}$.

In some embodiments of the invention, the Krebs cycle modulators comprise at least ashwagandha, eleuthero root (or extract), maca, L-arginine and L-citrulline, and at least vitamins $B_2$, $B_1$, $B_3$, $B_5$, and $B_9$.

In a preferred embodiment of the invention, the glutathione modulators of the invention induce the generation or proliferation of glutathione and/or a member of the glutathione family, including, without limitation, glutathione peroxidase, and/or catalase synthesis.

In some embodiments of the invention, the glutathione modulators comprise at least one of the aforementioned herbs, i.e., schisandra chinensis berry, epimedium, stinging nettle, yohimbe, red Korean ginseng, eleuthero root (or extract), damiana, ashwagandha and maca, at least one of the aforementioned metal ions, i.e., Fe and Cu, and one of the aforementioned B vitamins, i.e., vitamins $B_2$, $B_1$, $B_3$, $B_5$, $B_7$, $B_9$, and $B_{12}$.

In some embodiments of the invention, the glutathione modulators comprise at least schisandra chinensis berry, damiana, epimedium, maca, stinging nettle leaf, Fe, Cu, and at least vitamins $B_2$, $B_5$, $B_6$, and $B_7$.

In a preferred embodiment of the invention, the neurotransmitter modulators of the invention induce and/or modulate the generation of neurotransmitters and modulates the transmission thereof by and between neurons and, hence, cells.

In some embodiments of the invention, the neurotransmitter modulators comprise at least one of the aforementioned herbs, i.e., schisandra chinensis berry, epimedium, stinging nettle, yohimbe, red Korean ginseng, eleuthero root (or extract), damiana, ashwagandha and maca, at least one of the aforementioned biochemical agents, i.e., cannabidiol (CBD), and at least one of the aforementioned B vitamins, i.e., vitamins $B_2$, $B_1$, $B_3$, $B_5$, $B_7$, $B_9$, and $B_{12}$.

In some embodiments of the invention, the neurotransmitter modulators comprise at least epimedium, stinging nettle, maca, eleuthero root, yohimbe, cannabidiol (CBD), and at least vitamins $B_1$ and $B_6$.

In a preferred embodiment of the invention, the DNA modulators of the invention support and/or enhance mitochondrial DNA activity.

In a preferred embodiment, the DNA modulators support and/or enhance mitochondrial DNA activity by protecting and/or facilitating the repair of mitochondrial DNA.

In a preferred embodiment of the invention, the DNA modulators comprise, without limitation, vitamin $B_{12}$.

In a preferred embodiment of the invention, the endocannabinoid system modulators induce cell receptor activity.

In a preferred embodiment, the endocannabinoid system modulators induce cannabinoid receptor activity.

In a preferred embodiment, the endocannabinoid system modulators comprise cannabidiol (CBD) or a component thereof.

In some embodiments of the invention, the bioenergetic platforms further comprise a nuclear hormone receptor modulator.

In a preferred embodiment of the invention, the nuclear hormone receptor modulators induce cell receptor activity; preferably, nuclear hormone receptor modulator activity, e.g., the activity of nuclear hormone receptor modulators estrogen receptor-α (ERα), estrogen receptor-β (ERβ), androgen receptor (AR), and mineralocorticoid receptor (MR).

In some embodiments of the invention, the nuclear hormone receptor modulator comprises red Korean ginseng.

In a preferred embodiment of the invention, the vibrational energy platforms of the invention comprise at least one energy signature component comprising or derived from, without limitation, schisandra chinensis, damiana leaf, eleuthero root, stinging nettle, maca root, yohimbe root, epimedium, L-arginine, and L-citrulline.

The selection, function, and synergistic relationship by and between the biochemical scaffold platforms and modulators associated therewith will now be described in detail.

Vibrational Energy Platform

As indicated above and discussed in detail below, in a preferred embodiment of the invention, the vibrational energy platforms of the invention comprise at least one energy signature component derived from at least one herb, such as schisandra chinensis, or at least one biochemical agent, such as L-arginine.

It has been found, and Applicants have confirmed that specific, critical frequencies of radiation energy create an interaction by and between a selective herb or biochemical agent and a suitable medium; more particularly, by and between the herb or biochemical agent and electric dipole structures of water molecules in a glycerol water solution, whereby permanent polarization of the glycerol water molecules, i.e., coherent glycerol water molecules, is generated.

It has also been found and Applicants have also confirmed that water molecules behave as an "active" medium that can capture, replicate, and retain energy signatures of an herb or biochemical agent through defined harmonic oscillation frequencies. Indeed, Applicants have confirmed that highly specific short-range hydrogen bond and electric dipole-to-dipole static interactions between water molecules can be modulated by defined harmonic oscillation frequencies to generate quantum coherent water molecules (also referred to as "energetic blanks"), which form self-assembled coherence domains (CDs) that capture, replicate, and retain energy signatures of herbs and biochemical agents in energy blank regions of the coherence domains.

Figure 5:
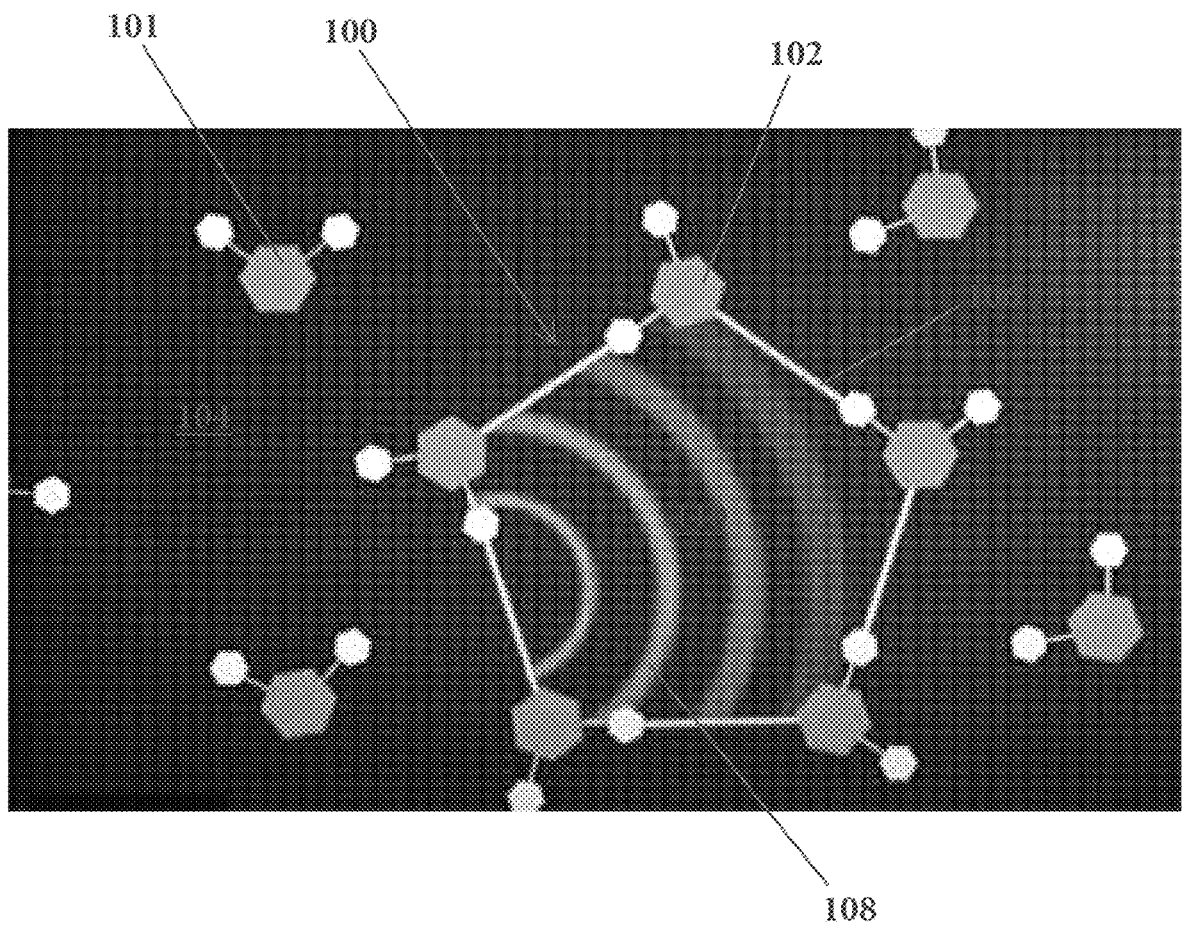
FIG. 5 is a schematic illustration of a coherent domain in a glycerol water solution.

Referring now to FIG. 5, there is shown a coherence domain 100 in a glycerol water solution 104 that comprises a series of quantum coherent water molecules 102, which are bound via short-range hydrogen bonds 106. As illustrated in FIG. 5, the coherence domain 100 comprises an energy signature 108 of a selective herb or biochemical agent that is retained within the energy blank region 110. The coherence domain 100 preferably oscillates in unison with the energy signature 108 retained within the energy blank region 110.

According to the invention, when at least one herb and/or biochemical agent of the invention and a glycerol water solution 104 are subjected to harmonic oscillation at a defined frequency range or sequential harmonic oscillation at defined frequency ranges for a defined, predetermined period of time, the water molecules 101 in the glycerol water solution 104 exhibit quantum coherence, whereby a plurality of distinct quantum coherent water molecules 102 and, hence, coherent domains 100, are generated in the glycerol water solution 104, and, thereby, a unique glycerol water solution (i.e., vibrational energy platform) comprising the following two separate and distinct forms of water molecules is formed: (i) complex, stable quantum coherent water molecules 102, i.e., "energetic blanks," and (ii) water molecules 101.

The quantum coherent water molecules 102 of the glycerol water solution 104, i.e., distinct energetic blanks, form coherent domains 100 that capture, replicate, and retain defined energy signatures 108 of the selective herb and/or biochemical agent of the invention and, hence, chemical components thereof in the energy blank region 110 of the coherence domains 100, i.e., the energy signature 108 of the selective herb and/or biochemical agent is imparted to, captured, replicated, and retained by the coherent domains 100 formed by the quantum coherent water molecules 102 of the glycerol water solution 104.

Applicants have found that when a glycerol water solution comprising coherent domains with a retained energy signature of a selective herb or biochemical agent, i.e., a biochemical scaffold, is in communication with biological tissue, i.e. delivered to a subject, the biochemical scaffold induces specific biochemical activities through resonant transfer of the retained energy signatures to the biological tissue and, hence, endogenous cells thereof, whereby a mechanism for the precise regulation of biochemical activities in vivo (based on the properties and function of the transferred energy signature) is provided.

By way of example, Applicants have found that when a glycerol water solution comprising coherent domains with a retained energy signature of ashwagandha is delivered to a subject and, hence, is in communication with the subject's biological tissue, the biochemical scaffold induces a plurality of seminal biological activities, including (i) facilitating lowered production of cortisol, (ii) balancing, i.e., modulating the release, of thyroid hormones, and (iii) reducing the breakdown of ATP through resonant transfer of the retained energy signature of ashwagandha to the biological tissue and, hence, endogenous cells thereof.

The resonant transfer of the retained energy signature of ashwagandha to the endogenous cells is conducted via a plurality of cell surface receptor proteins disposed on and in the cell membranes of endogenous cells, which communicate with the energy signature retained by the coherent domains and, thereby initiate the production of cytokines, transcription factors, extracellular vesicles, etc. by the endogenous cells that induce the noted biological activities induced by the retained energy signature of ashwagandha.

According to the invention, optimal and, hence, preferred harmonic oscillation parameters to achieve the above referenced biochemical activity by and between an herb and/or biochemical agent and a glycerol water solution, and induced in vivo biological activities of biological tissue are set forth in Table I below.

TABLE I

| Pattern | Frequency | Period of Time |
|---|---|---|
| Steady state/continuous | 102 GHz-250 GHz | 3-5 hours |
| Sequential | 0.9 kHz-1.5 kHz | 3-60 minutes; |
| | 9.5 kHz-10.5 kHz | 3-60 minutes; |
| | 9.5 kHz-11.0 kHz | 3-60 minutes; |
| | 0.01 kHz-0.03 kHz | 3-60 minutes; and |
| | 0.004 kHz-0.010 kHz | 3-60 minutes. |

In some embodiments of the invention, a vibrational energy platform comprising at least one selective herb and/or biochemical agent, i.e., energy signature components, and a glycerol water solution is subjected to harmonic oscillation at a frequency in the range of 102 GHz-250 GHz for a period of time in the range of 3-5 hours, whereby a plurality of distinct quantum coherent water molecules are generated in the glycerol water solution, and, thereby, a glycerol water solution comprising the following two separate and distinct forms of water molecules is similarly formed, i.e., (i) the complex, stable coherent glycerol water molecules and (ii) the glycerol water-soluble molecules.

In some embodiments of the invention, the vibrational energy platform referenced above is subjected to sequential harmonic oscillation at frequencies in the range of approximately 0.9-1.5 kHz, 9.5-10.5 kHz, 9.5-11.0 kHz, 0.01-0.03 kHz, and 0.004-0.010 kHz for a period of time in the range of 3-60 minutes per frequency range, whereby the aforementioned activities are similarly promoted or induced.

According to the invention, the distinct energetic blanks, i.e., water molecules of the glycerol water solution, that are generated via the harmonic oscillation(s) referenced above, comprise a defined energy signature of the selective herb and/or biochemical agent and, hence, chemical components thereof.

According to the invention, the coherent domains can be configured and adapted to capture, replicate, and retain energy signatures of any herb or biochemical agent of the invention.

As indicated above, the energy signature components preferably comprise or are derived from at least one of the following herbs: schisandra chinensis, damiana leaf, eleuthero root, stinging nettle, maca root, yohimbe root, red Korean ginseng, epimedium, and ashwagandha; and/or at least one of the aforementioned biochemical agents, e.g., the amino acids L-arginine and L-citrulline.

Bioenergetic Platform

As indicated above, in a preferred embodiment of the invention, the bioenergetic platforms of the invention comprise at least one Krebs cycle modulator, glutathione modulator, neurotransmitter modulator, DNA modulator, or endocannabinoid system modulator.

In some embodiments of the invention, the bioenergetic platforms comprise a Krebs cycle modulator and/or glutathione modulator and/or neurotransmitter modulator and/or DNA modulator and/or endocannabinoid system modulator.

Each of the noted modulators are discussed in detail below.

Krebs Cycle Modulators

As indicated above, according to the invention, the Krebs cycle modulators of the invention induce and/or modulate at least one Krebs cycle metabolic reaction, process and/or pathway, including, without limitation, Krebs cycle product inhibition and/or substrate availability.

As set forth in priority U.S. application Ser. Nos. 14/223,392 and 16/116,539, a seminal process associated with the Krebs cycle is the catabolism of carbohydrates, fats, and proteins, which results in the production of a two carbon organic product, i.e., acetate in the form of acetyl-CoA. Acetyl-CoA and two equivalents of water ($H_2O$) are consumed during the Krebs cycle, producing two equivalents of carbon dioxide ($CO_2$) and one equivalent of HS-CoA.

In addition, one complete cycle of the Krebs cycle converts three equivalents of nicotinamide adenine dinucleotide ($NAD^+$) into three equivalents of reduced $NAD^+$ (NADH), one equivalent of ubiquinone (Q) into one equivalent of reduced ubiquinone ($QH_2$), and one equivalent each of guanosine diphosphate (GDP) and inorganic phosphate (Pt) into one equivalent of guanosine triphosphate (GTP). The NADH and $QH_2$ generated during the Krebs cycle are in turn used by the oxidative phosphorylation pathway to generate energy-rich adenosine triphosphate (ATP).

A primary source of acetyl-CoA is carbohydrates, which are broken down by glycolysis to produce pyruvate. Pyruvate is decarboxylated by the enzyme pyruvate dehydrogenase to generate acetyl-CoA.

Regulation of the Krebs cycle is largely dependent upon product inhibition and substrate availability. For example, NADH, a product of all dehydrogenases in the cycle (with the exception of succinate dehydrogenase) inhibits pyruvate dehydrogenase, isocitrate dehydrogenase, α-ketoglutarate dehydrogenase, and citrate synthase. Acetyl-CoA inhibits pyruvate dehydrogenase, while succinyl-CoA inhibits alpha-ketoglutarate dehydrogenase and citrate synthase.

As indicated above, the Krebs cycle modulators of the invention are capable of inducing and/or modulating at least one Krebs cycle metabolic reaction, process and/or pathway, including, without limitation, product inhibition and/or substrate availability.

As also indicated above, in some embodiments of the invention, the Krebs cycle modulators comprise at least one herb selected from the group comprising, without limitation, schisandra chinensis berry, epimedium, stinging nettle, yohimbe, red Korean ginseng, eleuthero root (or extract), damiana, ashwagandha, and maca, at least one amino acid, such as, without limitation, L-arginine and L-citrulline, and at least one B vitamin selected from the group comprising vitamins $B_2$, $B_1$, $B_3$, $B_5$, $B_7$, $B_9$, and $B_{12}$.

In some embodiments of the invention, the Krebs cycle modulators comprise at least ashwagandha, eleuthero root (or extract), maca, at least one amino acid, such as, without limitation, L-arginine or L-citrulline, and at least vitamins $B_2$, $B_1$, $B_3$, $B_5$, and $B_9$.

According to the invention, in some embodiments, the Krebs cycle modulators of the invention modulate product and/or substrate availability. By way of example, in some embodiments, the Krebs cycle modulators comprise eleuthero root, which Applicants have found facilitates the formation of glucose-6-phosphate. As stated, glucose-6-phosphate eventually converts to pyruvate, which enters the Krebs cycle as Acetyl-CoA.

In some embodiments, the Krebs cycle modulator comprises at least eleuthero root, which also enhances the activity of succinate dehydrogenase, an enzyme that facilitates the formation of FAD to $FADH_2$. As indicated above, these processes aid in the generation of ATP.

In some embodiments, the Krebs cycle modulator comprises at least maca. Applicants have found that maca works synergistically with eleuthero root by inducing co-factor proliferation, which supports activation of the Krebs cycle.

Applicants have also found that maca also facilitates the production of super oxide dismutase, i.e., an important antioxidant. Intracellular super oxide dismutase converts a highly undesirable free radical known as superoxide to hydrogen peroxide and oxygen.

In some embodiments, the Krebs cycle modulator comprises at least ashwagandha, which facilitates the lowering of cortisol and balancing of thyroid hormones. Applicants have found that ashwagandha also reduces the breakdown of ATP.

In some embodiments of the invention, the Krebs cycle modulator comprises at least L-arginine or L-citrulline. Applicants have also found that L-arginine and L-citrulline facilitate the production of nitrous oxide. Nitrous oxide induces vasodilation and, hence, enhanced blood flow. The enhanced blood flow results in an increase in delivered $O_2$ and, thereby, enhanced cellular energy.

As indicated above, in some embodiments of the invention, the Krebs cycle modulators comprise and at least one B vitamin selected from the group comprising vitamins $B_2$, $B_1$, $B_3$, $B_5$, $B_7$, $B_9$, and $B_{12}$, more preferably, at least one B vitamin selected from the group comprising vitamins $B_1$, $B_2$, $B_3$, $B_5$, and $B_9$.

As is well established, vitamin $B_1$, i.e., thiamine, plays a central role in the generation of energy from carbohydrates. Vitamin $B_1$ is involved in RNA and DNA production, as well as nerve function. Vitamin $B_1$'s active form is a coenzyme called thiamine pyrophosphate (TPP), which converts pyruvate to acetyl Coenzyme A (CoA).

Vitamin $B_2$, i.e., riboflavin, is involved in energy production for the electron transport chain and catabolism of fatty acids, i.e., beta oxidation.

Vitamin $B_3$, i.e., niacin, is composed of two co-enzyme forms of niacin: nicotinamide adenine dinucleotide (NAD) and nicotinamide adenine dinucleotide phosphate (NADP). Both play an important role in energy transfer reactions in the metabolism of glucose, fat, and alcohol.

NAD carries $H_2$ and associated electrons during metabolic reactions, including the pathway from the Krebs cycle to the electron transport chain. NADP is a key coenzyme in lipid and nucleic acid synthesis.

Vitamin $B_5$, i.e., pantothenic acid, is also involved in the oxidation of fatty acids and carbohydrates. Coenzyme A, which can be synthesized from pantothenic acid, is involved in the synthesis of amino acids, fatty acids, ketones, cholesterol, phospholipids, steroid hormones, neurotransmitters, such as acetylcholine, and antibodies.

Vitamin $B_9$, i.e., folic acid, acts as a co-enzyme in the form of tetrahydrofolate (THF), which is involved in the transfer of single-carbon units in the metabolism of nucleic acids and amino acids. THF is involved in pyrimidine nucleotide synthesis, which is required for normal cell division. Folate also aids in erythropoiesis, i.e., the production of red blood cells.

Glutathione Modulators

As indicated above, according to the invention, the glutathione modulators of the invention induce (i) the generation or proliferation of glutathione and/or the glutathione family, including, without limitation, glutathione peroxidase, and/or (ii) catalase synthesis.

As also set forth in priority U.S. application Ser. Nos. 14/223,392 and 16/116,539, glutathione; specifically, glutathione peroxidase, is an important intracellular antioxidant that induces conversion of hydrogen peroxide to $H_2O$ and $O_2$. Glutathione reduces disulfide bonds formed within cytoplasmic proteins to cysteines by serving as an electron donor. In the process, glutathione is converted to its oxidized form glutathione disulfide (GSSG), as known as L-(-)-glutathione.

After oxidation, glutathione is reduced back to glutathione reductase, using NADPH as an electron donor.

As indicated above, in some embodiments of the invention, the glutathione modulators comprise at least one of the aforementioned herbs, i.e., schisandra chinensis berry, epimedium, stinging nettle, yohimbe, red Korean ginseng, eleuthero root (or extract), damiana, ashwagandha and maca, at least one of the aforementioned metal ions, i.e., Fe and Cu, and at least one of the aforementioned B vitamins, i.e., vitamins $B_2$, $B_1$, $B_3$, $B_5$, $B_7$, $B_9$ and $B_{12}$.

In some embodiments of the invention, the glutathione modulators comprise at least schisandra chinensis berry, damiana and epimedium, maca, stinging nettle, and at least vitamins $B_2$, $B_5$, $B_6$, and $B_7$.

In some embodiments of the invention, the glutathione modulators further comprise Fe and/or Cu.

As indicated above, vitamin $B_2$, i.e., riboflavin, facilitates energy production for the electron transport chain and catabolism of fatty acids, i.e., beta oxidation.

As also indicated above, in some embodiments of the invention, the glutathione modulator is effective to induce the synthesis of catalase, another key antioxidant. In these embodiments, the glutathione modulator can comprise, without limitation, maca, stinging nettle, metal ions selected from the group comprising Fe and Cu, and B-vitamins selected from the group comprising vitamins $B_2$, $B_5$, $B_6$, and $B_7$.

Vitamin $B_6$, i.e., pyridoxine, is stored in the body as pyridoxal 5'-phosphate (PLP), which is the co-enzyme form of vitamin $B_6$. Pyridoxine is also involved in the metabolism of amino acids and lipids; in the synthesis of neurotransmitters and hemoglobin, as well as in the production of nicotinic acid (vitamin $B_3$). Pyridoxine also plays an important role in gluconeogenesis.

Vitamin $B_7$, i.e., biotin, also plays a key role in the metabolism of lipids, proteins, and carbohydrates. It is a critical co-enzyme of four carboxylases: (i) acetyl CoA carboxylase, which is involved in the synthesis of fatty acids from acetate; (ii) propionyl CoA carboxylase, which is involved in gluconeogenesis; (iii) β-methylcrotonyl CoA carboxylase, which is involved in the metabolism of leucin; and (iv) pyruvate CoA carboxylase, which is involved in the metabolism of energy, amino acids, and cholesterol.

Neurotransmitter Modulators

Figure 3:
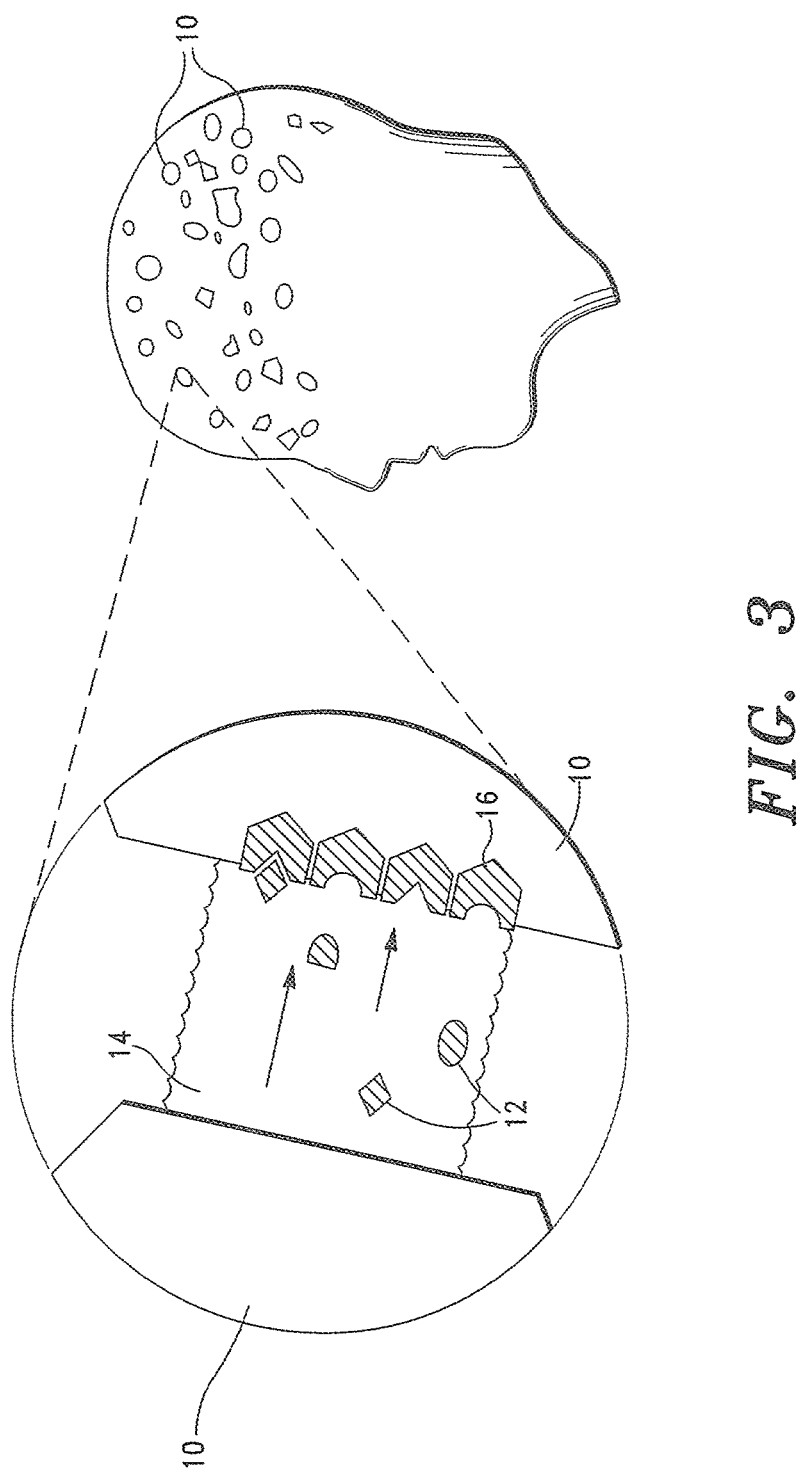
FIG. 3 is a schematic illustration of electrochemical signal transmission.

It is well established that the human brain contains large numbers of highly specialized cells called neurons. As illustrated in FIG. 3, the neurons 10 connect to and communicate with other neurons and, hence, cells via neurotransmitters 12, i.e., endogenous electrochemical signals, over synapses 14.

As further illustrated in FIG. 3 and discussed in detail below, when a sender neuron 10 generates and transmits neurotransmitters 12, the neurotransmitters 12 activate target receptors 16 on the receiver neuron 10 and, hence, initiates at least one seminal biological activity conducted by receiver neuron 10.

According to the invention, the neurotransmitter modulators of the invention induce (and/or modulate) the generation and proliferation of neurotransmitters and modulate the transmission thereof by and between neurons.

A key neurotransmitter is acetylcholine (ACh). Acetylcholine stimulates the central nervous system to enhance mental acuity, i.e., learning ability, short term memory and mental focus.

Another key neurotransmitter is dopamine. Dopamine functions as an inhibitory and excitatory neurotransmitter. As inhibitory neurotransmitter, it causes balance and general sense of well-being. As excitatory neurotransmitter, it improves cognition, concentration, and focus.

A further key neurotransmitter is norepinephrine, which effects cognition, mood and mental concentration.

As indicated above, the neurotransmitter modulators of the invention induce the generation or proliferation of at least one neurotransmitter, including ACh, dopamine, and norepinephrine, and/or the transmission thereof by and between neurons.

As also indicated above, in some embodiments of the invention, the neurotransmitter modulators comprise least one of the aforementioned herbs, i.e., schisandra chinensis berry, epimedium, stinging nettle, yohimbe, red Korean ginseng, eleuthero root (or extract), damiana, ashwagandha and maca, at least one biochemical agent, i.e., cannabidiol (CBD), and at least one of the aforementioned B vitamins, i.e., vitamins $B_2$, $B_1$, $B_3$, $B_5$, $B_7$, $B_9$, and $B_{12}$.

In some embodiments of the invention, the neurotransmitter modulators comprise at least epimedium, stinging nettle, maca, eleuthero root, yohimbe, cannabidiol (CBD), and at least vitamins $B_1$ and $B_6$.

Applicants have found that stinging nettle increases the level of neurotransmitters available to act on the neuron receptors; particularly, dopamine and acetylcholine, thus improving several mental processes, e.g., learning and recollection abilities.

Maca supports acetyl cholinesterase and, thereby, similarly enhances the proliferation of acetylcholine.

Applicants have further found that, in addition to the Krebs cycle functions discussed above, eleuthero root enhances neuron activities, e.g., short term memory.

Yohimbe is a pre- and post-synaptic, alpha-2 adrenergic blocker that enhances neurotransmitter release and, thereby, enhanced cognitive functioning.

Yohimbe also induces elevation of norepinephrine from the locus coeruleus, resulting in enhanced memory. It has also been found that Yohimbe can abate one or more symptoms associated with post-traumatic stress disorder (PTSD).

Applicants have additionally found that the synergistic effect by and between maca and eleuthero root also provides cellular balance and decreases the negative effects of stress.

Epimedium, which includes the active element icariin, lowers the amyloid precursor protein (APP) level and, hence, reduces amyloid beta peptide (AB). Tau proteins are used in the brain as axonal microtubule stabilizers. However, when the Tau proteins are hyperphosphorylated via glycogen synthase kinase-3 (GSK-3), amyloid beta proteins are generated, and Alzheimer issues arise. The hyperphosphorylation of Tau proteins is initiated in the locus coeruleus. Icariin abates hyperphosphorylation and, thus, reduces AB generation.

Icariin is also an acetylcholinesterase inhibitor. Thus, more acetylcholine is available for memory and cognitive functions.

As discussed in detail below, cannabidiol (CBD) activates CB1 and CB2 receptors of the endocannabinoid system. By activating the CB1 and CB2 receptors the neurochemical consequences of the beta-amyloid proteins are reduced, which reduces inflammatory activity associated therewith.

DNA Modulators

According to the invention, the DNA modulators of the invention support and/or enhance mitochondrial DNA activity by, among other activities, protecting and/or facilitating the repair of mitochondrial DNA.

As indicated, mammalian mitochondria are organelles that produce more than 90% of cellular ATP. In addition to supplying ATP, i.e., cellular energy, mitochondria are also involved in other cellular mechanisms, including cellular differentiation, apoptosis, as well as cell cycle modulation and cell growth.

When a cell has temporarily or reversibly stopped dividing or regenerating it is often deemed to have entered a quiescent or senescent state referred to as the $G_0$ phase of the cell cycle.

Non-proliferative cells generally enter the senescent $G_0$ phase or state from the $G_1$ phase and may remain senescent for long periods of time, possibly indefinitely (as is often the case for neurons). Senescence is very common for "adult" cells that are fully differentiated.

The maximum number of cell divisions that a cell can undergo, varies from cell type to cell type and organism. In fibroblasts, this number is about 50 divisions, after which cell division ceases.

However, some cells become senescent after fewer replication cycles as a result of DNA damage or degradation, e.g., DNA mutations, DNA oxidation, and chromosome losses, which would make a cell's progeny nonviable. If the DNA damage cannot be easily repaired, the cells either prematurely age or self-destruct (i.e., apoptosis or programmed cell death).

The process of cellular senescence can also be triggered by several additional mechanisms, including telomere shortening (i.e., a form of DNA damage or degradation).

Due to DNA replication mechanisms and oxidative stress, telomeres become progressively shorter with each round of replication. As increasing numbers of cell division occur, the telomeres reach a critically short length, which present as double-stranded DNA breaks, resulting in telomere-initiated senescence.

Protecting and/or facilitating the repair of mitochondrial DNA, which can be achieved by virtue of the DNA modulators of the invention, is thus essential to achieve optimal cell function and, thereby, physiological functioning. Healthy mitochondrial DNA also provides healthy enzymatic processes, which are required for oxidative phosphorylation and, hence, continued energy production.

As indicated above, the DNA modulators of the invention support mitochondrial DNA by protecting and/or facilitating the repair of mitochondrial DNA.

In a preferred embodiment of the invention, the DNA modulators of the invention comprise vitamin $B_{12}$.

According to the invention, $B_{12}$ supports DNA activity; specifically, synthesis and, in some instances, prevents and, thereby, inhibits megaloblastic anemia.

Vitamin $B_{12}$ is also involved in the cellular metabolism of carbohydrates, proteins, and lipids. It functions as a co-enzyme in intermediary metabolism for the methionine synthase reaction with methylcobalamin, and the methylmalonyl CoA mutase reaction with adenosylcobalamin.

Endocannabinoid System Modulators

According to the invention, the endocannabinoid system modulators of the invention induce cell receptor activity; preferably, cannabinoid receptor activity, i.e., receptors CB1 or CB2.

In a preferred embodiment of the invention, the endocannabinoid system modulators comprise cannabidiol (CBD).

CBD is one of many cannabinoid molecules produced by plants from the genus *Cannabis*, second only to THC in abundance.

CBD activates the two seminal cannabinoid receptors (CB1 and CB2) and, hence, as discussed below, induces several significant physiological activities. One significant physiological activity induced by activating the CB1 and CB2 receptors is modulation of inflammatory activity and diseases associated therewith, e.g., arthritis. The inflammation modulation, i.e., reduction thereof, is achieved by (among other factors) reducing the neurochemical effects of beta-amyloid proteins and, thereby, reactive oxidative stress and reactive oxygen.

As discussed below, in addition to activating the CB1 and CB2 receptors, CBD can, and in many instances will, enhance the levels of naturally-produced endocannabinoids, e.g., anandamide and 2-arachidonoyl glycerol (2-AG), by inhibiting the enzymes that break them down.

CBD also activates multiple serotonin receptors in the brain; particularly, serotonin 1A receptors. As a result, CBD can ameliorate various disorders, including neuropathic pain and motivational disorders, such as depression and anxiety.

CBD also modulates opioid receptor activity. As is well known in the art, opioid receptors are the key targets of pharmaceutical pain killers and drugs of abuse, such as morphine, heroin, and fentanyl. CBD's ability to modulate opioid receptor activity and enhance the activation of serotonin 1A receptors dampens drug cravings and, hence, can, and in many instances will, abate drug dependence; particularly, opioid and heroin dependence.

Applicants have found that, in addition to an endocannabinoid system modulator, CBD is also an effective neurotransmitter modulator. As indicated above, CBD activates the two seminal cannabinoid receptors CB1 and CB2. By activating the CB1 receptors, anandamide is increased and the associated elevation of corticosterone (stress hormone) and 2-arachidonoyl glycerol (2-AG) are reduced, which have a direct effect (and in many instances a calming effect) on the amygdala, i.e., emotional center.

Although CBD is a cannabinoid, CBD does not directly interact with and, hence, activate the CB1 and CB2 receptors. Instead, CBD indirectly activates the CB1 and CB2 receptors by modulating signaling through the CB1 and CB2 receptors by inhibiting the enzyme fatty acid amide hydrolase (FAAH). FAAH inactivates anandamide and also converts 2-AG to mono acylglycerol. By inhibiting FAAH more of anandamide and 2-AG available, which further enhances the calming effect on the amygdala.

Nuclear Hormone Receptor Modulators

As indicated above, according to the invention, the nuclear hormone receptor modulators of the invention induce cell receptor activity; preferably, nuclear hormone receptor modulator activity, e.g., the activity of nuclear hormone receptor modulators estrogen receptor-α (ERα), estrogen receptor-β (ERβ), androgen receptor (AR), and mineralocorticoid receptor (MR).

In one preferred embodiment of the invention, the nuclear hormone receptor modulator comprises red Korean ginseng, which comprises a plurality of ginsenosides, including, without limitation, ginsenoside Rb-1, ginsenoside Rg-1, ginsenoside Re, ginsenoside Rg3, ginsenoside Rg5, ginsenoside Rh2, ginsenoside Rh1, ginsenoside Rh3, ginsenoside Rh4, ginsenoside Rs3, ginsenoside Rb-2, ginsenoside Rd, ginsenoside Rp-1, and ginsenoside F4.

As is well established, ginsenosides (also referred to as "panaxosides") are classified as both steroid glycosides and triterpene saponins. Ginsenosides are derived exclusively from plants belonging to the genus *Panax* (i.e., ginseng), and exhibit a multitude of biological effects that mimic seminal biological activities of anti-inflammatory steroidal drugs that bind to and activate nuclear hormone receptors. Ginsenosides are thus lipophilic in nature, and by virtue of their steroidal backbone, they can traverse cell membranes of mammalian cells by simple diffusion and regulate cellular functions by binding to specific intracellular target proteins in the cytoplasm and nucleus of the mammalian cells.

It has also been found and Applicants have confirmed that ginsenosides activate seminal nuclear hormone receptors (e.g., ERα, ERβ, AR, and MR) and, hence, as discussed below, induce several significant physiological activities. One significant physiological activity induced by activating the nuclear hormone receptors is the modulation of inflammatory activity and diseases associated therewith, e.g., colitis, alcohol-induced hepatitis, ischemia/reperfusion (IR) injury, neurodegenerative diseases, and impaired memory diseases. The modulation of inflammatory activity, i.e., reduction thereof, is achieved by (among other factors) suppressing the production of seminal proinflammatory cytokines and, thereby modulating the activities of inflammatory signaling pathways, such as nuclear factor-κB (NF-κB) and activator protein-1 signaling pathways.

Ginsenoside Rb1 inhibits TNF-α production in macrophages and suppresses the activation of NF-κB, which is a key regulator of inflammatory activity, as well as a modulator of tumor necrosis factor-α (TNF-α) production in macrophages. Ginsenoside Rb1 also significantly reduces activation of interleukin-1 (IL-1) receptor-associated kinase (IRAK-1), which is an inhibitor of κB (IκB) kinase (IKK)-α, NF-κB, and mitogen-activated protein kinases (MAPKs).

Ginsenosides also exhibit seminal neuroprotective effects by modulating, i.e., reducing inflammatory activity in the brain and in the central nervous system (CNS). Ginsenoside Rd reduces inflammatory activity in the brain and CNS by regulating free radical scavenging pathways and reducing inflammatory responses in late-stage ischemia by the inhibiting the expression of inducible nitric oxide synthase (iNOS) and prostaglandin-endoperoxide synthase 2 (COX-2).

As is well established, lipopolysaccharide (LPS)-induced inflammatory activity is associated with neurodegenerative diseases, including Parkinson disease, Alzheimer's disease (AD), and multiple sclerosis (MS). LPS compounds activate microglial cells in the brain and CNS that promote and induce inflammatory activities associated with the noted neurodegenerative diseases. Ginsenoside Re reduces inflammatory activity in the brain and CNS by inhibiting proinflammatory mediators (iNOS and COX2) that are generated in response to mammalian cell exposure to LPS and inhibiting activation of the p38-MAPK signaling pathway in microglial cells.

Ginsenoside Rg1 similarly modulates microglial cell activation by reducing the production of TNF-α and NO as well as the expression of iNOS and ionized calcium-binding adapter molecule 1 (Iba-1) by inhibiting the activation of NF-κB and MAPKs pathways.

It has also been found that ginsenoside Rg1 also facilitates protection of other biological tissues, e.g., hepatic tissue, from ischemia/reperfusion (IR) injury by reducing inflammatory activity and associated apoptosis events resulting therefrom by modulating NF-κB and ROS-NO-hypoxia-inducible factor signaling pathways. IR injury; more particularly, IR injury of the brain and CNS is also ameliorated via Ginsenoside Rg1 mediated activation of peroxisome proliferator-activated receptor-γ/heme oxygenase-1 (HO-1), suppression of protease-activated receptor-1 expression, and inhibition of mitogen-activated protein kinase 14 (p38α MAPK), and, hence, inhibited activation of the p38-MAPK cell signaling pathway.

The biochemical scaffolds of the invention thus modulate various seminal molecular activities, including inducing (i) at least one Krebs cycle metabolic reaction, process and/or pathway, (ii) generation or proliferation of glutathione and/or a member of the glutathione family, (iii) generation or proliferation of at least one neurotransmitter, and/or modulating the transmission thereof by and between neurons, (iv) inducing and/or supporting mitochondrial DNA activity, and (v) cell receptor activity.

The biochemical scaffolds of the invention can thus comprise various combinations of herbs, vitamins, amino acids, glutathione, and other biochemical and bioactive agents.

The biochemical scaffolds of the invention can further comprise a cofactor, including, without limitation, organic cofactors, such as flavin and heme, and inorganic cofactor, such as the metal ions $Mg^{2+}$, $Cu^{+}$, $Mn^{2+}$, and iron-sulfur clusters.

In one embodiment, the biochemical scaffold comprises the herbs and vitamins set forth in Table II below.

TABLE II

| Vitamin/Herb | Mg per oz. of liquid medium |
| --- | --- |
| yohimbe | 650-1950 |
| epimedium | 650-1950 |
| ashwagandha | 650-1950 |
| cannabidiol (CBD) | 5-20 |
| vitamin $B_{12}$ | 0.2-0.5 |

In some embodiments, the biochemical scaffold comprises the herbs and vitamins set forth in Table III below.

TABLE III

| Vitamin/Herb | Mg per oz. of liquid medium |
| --- | --- |
| schisandra chinensis | 1175-2350 |
| yohimbe | 650-1950 |
| epimedium | 650-1950 |
| ashwagandha | 650-1950 |
| cannabidiol (CBD) | 227-936 |
| vitamin $B_{12}$ | 198-482 |

In another embodiment, the biochemical scaffold comprises the herbs and vitamins set forth in Table IV below.

TABLE IV

| Vitamin/Herb | Mg* |
| --- | --- |
| epimedium | 1175-2350 |
| stinging nettle | 1175-2350 |
| yohimbe | 1175-2350 |
| red Korean ginseng | 1175-2350 |
| eleuthero root | 1175-2350 |
| damiana | 1175-2350 |
| ashwagandha | 1175-2350 |
| maca | 1175-2350 |
| L-arginine | 1175-2350 |
| vitamin $B_1$ | 1.0-2.0 |
| vitamin $B_2$ | 1.0-2.0 |
| vitamin $B_3$ | 15-25 |
| vitamin $B_5$ | 15-25 |
| vitamin $B_6$ | 3.0-5.0 |
| vitamin $B_7$ | 0.10-1.0 |
| vitamin $B_9$ | 0.30-1.2 |
| vitamin $B_{12}$ | 2.0-3.2 |

*In a glycerin based liquid medium comprising 235 ml to 245 ml.

According to the invention, there are thus provided methods for modulating cellular activity of a subject comprising the steps of:
 (i) forming and, hence, providing a liquid composition comprising a liquid medium, a bioenergetic platform of the invention, and a vibrational energy platform of the invention;
 (ii) subjecting the liquid composition to harmonic oscillation at a frequency in the range of 102 GHz to 250 GHz for a period of time in the range of 3 hours to 5 hours, wherein a liquid biochemical scaffold is provided; and
 (iii) delivering a therapeutically effective amount of the liquid biochemical scaffold to the subject.

According to the invention, there are also provided methods for modulating cellular activity of a subject comprising the steps of:
 (i) forming and, hence, providing a liquid composition comprising a liquid medium, a bioenergetic platform of the invention, and a vibrational energy platform of the invention;
 (ii) subjecting said liquid composition to sequential harmonic oscillation at a first frequency in the range of 0.9 kHz-1.5 kHz for a first period of time in the range of 3-60 minutes, a second frequency in the range of 9.5 kHz-10.5 kHz for a second period of time in the range of 3-60 minutes, a third frequency in the range of 9.5 kHz-11.0 kHz for a third period of time in the range of 3-60 minutes, a fourth frequency in the range of 0.01 kHz-0.03 kHz for a fourth period of time in the range of 3-60 minutes, and a fifth frequency in the range of 0.004 kHz-0.010 kHz for a fifth period of time in the range of 3-60 minutes, wherein a liquid biochemical scaffold is provided; and
 (iii) delivering a therapeutically effective amount of the liquid biochemical scaffold to the subject.

In one embodiment of the invention, there is thus provided a method for modulating cellular activity of a subject comprising the steps of:
 (i) forming and, hence, providing a liquid composition comprising glycerin-based water, schisandra chinensis, yohimbe, epimedium, ashwagandha, cannabidiol (CBD), and vitamin $B_{12}$;
 (ii) subjecting the liquid composition to harmonic oscillation at a frequency in the range of 102 GHz to 250 GHz for a period of time in the range of 3 hours to 5 hours, wherein a liquid biochemical scaffold is provided; and (iii) delivering a therapeutically effective amount of the liquid biochemical scaffold to the subject.

In some embodiments of the invention, the method for modulating cellular activity of a subject comprises the steps of:
(i) forming and, hence, providing a liquid composition comprising glycerin-based water, schisandra chinensis, yohimbe, epimedium, ashwagandha, cannabidiol (CBD), and vitamin $B_{12}$;
(ii) subjecting said liquid composition to sequential harmonic oscillation at a first frequency in the range of 0.9 kHz-1.5 kHz for a first period of time in the range of 3-60 minutes, a second frequency in the range of 9.5 kHz-10.5 kHz for a second period of time in the range of 3-60 minutes, a third frequency in the range of 9.5 kHz-11.0 kHz for a third period of time in the range of 3-60 minutes, a fourth frequency in the range of 0.01 kHz-0.03 kHz for a fourth period of time in the range of 3-60 minutes, and a fifth frequency in the range of 0.004 kHz-0.010 kHz for a fifth period of time in the range of 3-60 minutes, wherein a liquid biochemical scaffold is provided; and
(iii) delivering a therapeutically effective amount of the liquid biochemical scaffold to the subject.

In another embodiment of the invention, there is also provided a method of modulating cellular activity of a subject, comprising the steps of:
(i) forming and, hence, providing a liquid composition comprising glycerin-based water, schisandra chinensis, eleuthero root, epimedium, maca root, cannabidiol (CBD), vitamin $B_1$, vitamin $B_2$, vitamin $B_3$, vitamin $B_5$, vitamin $B_6$, vitamin $B_7$, and vitamin $B_{12}$;
(ii) subjecting the liquid composition to harmonic oscillation at a frequency in the range of approximately 102 GHz to 250 GHz for a period of time in the range of approximately 3 hours to 5 hours, wherein a liquid biochemical scaffold is provided; and
(iii) delivering a therapeutically effective amount of the liquid biochemical scaffold to the subject.

In some embodiments of the invention, the method for modulating cellular activity of a subject comprises the steps of:
(i) forming and, hence, providing a liquid composition comprising glycerin-based water, schisandra chinensis, eleuthero root, epimedium, maca root, cannabidiol (CBD), vitamin $B_1$, vitamin $B_2$, vitamin $B_3$, vitamin $B_5$, vitamin $B_6$, vitamin $B_7$, and vitamin $B_{12}$;
(ii) subjecting the liquid composition to sequential harmonic oscillation at a first frequency in the range of approximately 0.9 kHz-1.5 kHz for a first period of time in the range of approximately 3-60 minutes, a second frequency in the range of approximately 9.5 kHz-10.5 kHz for a second period of time in the range of approximately 3-60 minutes, a third frequency in the range of approximately 9.5 kHz-11.0 kHz for a third period of time in the range of approximately 3-60 minutes, a fourth frequency in the range of approximately 0.01 kHz-0.03 kHz for a fourth period of time in the range of approximately 3-60 minutes, and a fifth frequency in the range of approximately 0.004 kHz-0.010 kHz for a fifth period of time in the range of approximately 3-60 minutes, wherein a liquid biochemical scaffold is provided; and
(iii) delivering a therapeutically effective amount of the liquid biochemical scaffold to the subject.

In some embodiments of the invention, the method for modulating cellular activity of a subject comprises the steps of:
(i) forming and, hence, providing a liquid composition comprising glycerin-based water, epimedium, stinging nettle, yohimbe, red Korean ginseng, eleuthero root, damiana, ashwagandha, maca root, vitamin $B_1$, vitamin $B_2$, vitamin $B_3$, vitamin $B_5$, vitamin $B_6$, vitamin $B_7$, vitamin $B_9$, and vitamin $B_{12}$;
(ii) subjecting the liquid composition to sequential harmonic oscillation at a first frequency in the range of approximately 0.9 kHz-1.5 kHz for a first period of time in the range of approximately 3-60 minutes, a second frequency in the range of approximately 9.5 kHz-10.5 kHz for a second period of time in the range of approximately 3-60 minutes, a third frequency in the range of approximately 9.5 kHz-11.0 kHz for a third period of time in the range of approximately 3-60 minutes, a fourth frequency in the range of approximately 0.01 kHz-0.03 kHz for a fourth period of time in the range of approximately 3-60 minutes, and a fifth frequency in the range of approximately 0.004 kHz-0.010 kHz for a fifth period of time in the range of approximately 3-60 minutes, wherein a liquid biochemical scaffold is provided; and
(iii) delivering a therapeutically effective amount of the liquid biochemical scaffold to the subject.

In some embodiments of the invention, the method for modulating cellular activity of a subject comprises the steps of:
(i) forming and, hence, providing a liquid composition comprising in the range of approximately 235 ml to 245 ml, the liquid composition comprising glycerin-based water, epimedium in the range of approximately 1175.0 mg to 2350.0 mg, stinging nettle in the range of approximately 1175.0 mg to 2350.0 mg, yohimbe in the range of approximately 1175.0 mg to 2350.0 mg, red Korean ginseng in the range of approximately 1175.0 mg to 2350.0 mg, eleuthero root in the range of approximately 1175.0 mg to 2350.0 mg, damiana in the range of approximately 1175.0 mg to 2350.0 mg, ashwagandha in the range of approximately 1175.0 mg to 2350.0 mg, maca root in the range of approximately 1175.0 mg to 2350.0 mg, vitamin $B_1$ in the range of approximately 1.0 mg to 2.0 mg, vitamin $B_2$ in the range of approximately 1.0 mg to 2.0 mg, vitamin $B_3$ in the range of approximately 15.0 mg to 25.0 mg, vitamin $B_5$ in the range of approximately 15.0 mg to 25.0 mg, vitamin $B_6$ in the range of approximately 3.0 mg to 5.0 mg, vitamin $B_7$ in the range of approximately 100.0 mcg to 1.0 mg, vitamin $B_9$ in the range of approximately 300.0 mcg to 1.2 mg, and vitamin $B_{12}$ in the range of approximately 2.0 mg to 3.2 mg;
(ii) subjecting the liquid composition to sequential harmonic oscillation at a first frequency in the range of approximately 0.9 kHz-1.5 kHz for a first period of time in the range of approximately 3-60 minutes, a second frequency in the range of approximately 9.5 kHz-10.5 kHz for a second period of time in the range of approximately 3-60 minutes, a third frequency in the range of approximately 9.5 kHz-11.0 kHz for a third period of time in the range of approximately 3-60 minutes, a fourth frequency in the range of approximately 0.01 kHz-0.03 kHz for a fourth period of time in the range of approximately 3-60 minutes, and a fifth frequency in the range of approximately 0.004 kHz-0.010 kHz for a fifth period of time in the range of approximately 3-60 minutes, wherein a liquid biochemical scaffold is provided; and (iii) delivering a therapeutically effective amount of the liquid biochemical scaffold to the subject.

In a preferred embodiment, the therapeutically effective amount of the biochemical scaffold delivered to the subject comprises in the range of approximately 0.0006 oz. to 0.018 oz. of the biochemical scaffold.

According to the invention, the biochemical scaffolds of the invention can be processed in various manners. In one preferred embodiment of the invention, the biochemical scaffold is processed as follows:

(i) glycerin and distilled water are initially combined to form a first glycerol water solution;

(ii) extraneous energy signatures are removed from the first glycerol water solution by, for example, a Remedy Maker apparatus;

(iii) at least one of the aforementioned combinations and concentrations of B vitamins, i.e., vitamins $B_1$, $B_2$, $B_3$, $B_5$, $B_6$, $B_7$, $B_9$, and/or $B_{12}$, is added to the first glycerol water solution to form a vitamin solution;

(iv) glycerin and distilled water are then combined to form a second glycerol water solution;

(v) at least one of the aforementioned concentrations of herbs and biochemical agents, e.g., epimedium, stinging nettle, yohimbe, red Korean ginseng, eleuthero root, damiana, ashwagandha, maca, and/or L-arginine, is added to the second glycerol water solution to form a biochemical scaffold template solution;

(vi) the vitamin solution is oscillated at 700 cycles per minutes for 5-15 minutes to mix and/or solubilize the vitamin solution;

(vii) the vitamin solution is sequentially harmonically oscillated at a first frequency of approximately 0.99 kHz (999 Hz) for a period of time in the range of approximately 5-60, a second frequency of approximately 9.9 kHz (9,999 Hz) for a period of time in the range of approximately 5-60 minutes, a third frequency of approximately 10 kHz (10,000 Hz) for a period of time in the range of approximately 5-60 minutes, a fourth frequency of approximately 0.02 kHz (20 Hz) for a period of time in the range of approximately 5-60 minutes, and a fifth frequency of approximately 0.007 kHz (7.7 Hz) for a period of time in the range of approximately 5-60 minutes; and (viii) the energy signatures from the at least one of the aforementioned concentrations of herbs and biochemical agents from the biochemical scaffold template solution are transferred to the vitamin solution by, for example, the Remedy Maker apparatus, to the vitamin solution, whereby a biochemical scaffold liquid composition is formed.

As set forth in priority U.S. application Ser. No. 14/223,392, the biochemical scaffolds of the invention can be delivered to host tissue by various conventional means, including, without limitation, oral, sublingual, nasal, direct injection, topical application, etc.

As will readily be appreciated by one having ordinary skill in the art, the present invention provides numerous advantages compared to prior art formulations and methods for enhancing cell function and, thereby physiological performance. Among the advantages are the following:

The provision of biochemical scaffolds that enhance cell activity and function and, thereby, physical, and mental function, by inducing at least one Krebs cycle metabolic reaction, process and/or pathway.

The provision of biochemical scaffolds that enhance cell activity and function and, thereby, physical and mental function, by inducing production of $CO_2$, acetyl-CoA, $FADH_2$, and adenosine triphosphate (ATP).

The provision of biochemical scaffolds that enhance cell activity and function and, thereby, physical and mental function, by inducing the enhanced generation of neurotransmitters and/or modulating the transmission thereof by and between neurons.

The provision of biochemical scaffolds that enhance cell activity and function and, thereby, physical and mental function, by inducing cell receptor activity.

The provision of biochemical scaffolds that enhance cell activity and function and, thereby, physical and mental function, by inducing cell receptor activity.

The provision of biochemical scaffolds that enhance cell activity and function and, thereby, physical and mental function, by modulating the endocannabinoid system.

The provision of biochemical scaffolds that enhance cell activity and function and, thereby, physical and mental function, by inducing and/or modulating mitochondria DNA activity.

The provision of biochemical scaffolds that induce generation and/or proliferation of glutathione and/or a member of the glutathione family and, thereby, conversion of hydrogen peroxide to $H_2O$ and $O_2$.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A method of modulating cellular activity of a subject, consisting essentially of the steps:

(i) forming a liquid composition consisting of glycerin-based water, epimedium in the range of from about 1175.0 mg to about 2350.0 mg, stinging nettle in the range of from about 1175.0 mg to about 2350.0 mg, yohimbe in the range of from about 1175.0 mg to about 2350.0 mg, red Korean ginseng in the range of from about 1175.0 mg to about 2350.0 mg, eleuthero root in the range of from about 1175.0 mg to about 2350.0 mg, damiana in the range of from about 1175.0 mg to about 2350.0 mg, ashwagandha in the range of from about 1175.0 mg to about 2350.0 mg, maca root in the range of from about 1175.0 mg to about 2350.0 mg, vitamin $B_1$ in the range of from about 1.0 mg to about 2.0 mg, vitamin $B_2$ in the range of from about 1.0 mg to about 2.0 mg, vitamin $B_3$ in the range of from about 15.0 mg to about 25.0 mg, vitamin $B_5$ in the range of from about 15.0 mg to about 25.0 mg, vitamin $B_6$ in the range of from about 3.0 mg to about 5.0 mg, vitamin $B_7$ in the range of from about 100.0 mcg to about 1.0 mg, vitamin $B_9$ in the range of from about 300.0 mcg to about 1.2 mg, and vitamin $B_{12}$ in the range of from about 2.0 mg to about 3.2 mg, said liquid composition consisting in the range of from about 235 ml to about 245 ml;

(ii) subjecting said liquid composition to sequential harmonic oscillation at a first frequency in the range of 0.9 kHz-1.5 kHz for a first period of time in the range of 3-60 minutes, a second frequency in the range of 9.5 kHz-10.5 kHz for a second period of time in the range of 3-60 minutes, a third frequency in the range of 9.5 kHz-11.0 kHz for a third period of time in the range of 3-60 minutes, a fourth frequency in the range of 0.01 kHz-0.03 kHz for a fourth period of time in the range of 3-60 minutes, and a fifth frequency in the range of 0.004 kHz-0.010 kHz for a fifth period of time in the range of 3-60 minutes, wherein a liquid biochemical scaffold is provided; and (iii) delivering a therapeutically effective amount of said liquid biochemical scaffold to said subject, said therapeutically effective amount comprising in the range of approximately 0.0006 oz. to 0.018 oz. of said liquid biochemical scaffold.

* * * * *